(12) United States Patent
Yee

(10) Patent No.: US 7,069,084 B2
(45) Date of Patent: Jun. 27, 2006

(54) METHOD AND APPARATUS FOR PREVENTING AND TREATING EYELID PROBLEMS

(75) Inventor: Richard W. Yee, Houston, TX (US)

(73) Assignee: SeeFit Incorporated, Houston, TX (US)

( * ) Notice: Subject to any disclaimer, the term of this patent is extended or adjusted under 35 U.S.C. 154(b) by 510 days.

(21) Appl. No.: 10/172,426

(22) Filed: Jun. 14, 2002

(65) Prior Publication Data

US 2003/0233135 A1 Dec. 18, 2003

(51) Int. Cl.
*A61N 1/18* (2006.01)

(52) U.S. Cl. .......................... 607/53; 607/46; 607/141; 607/48

(58) Field of Classification Search .................... 607/48, 607/53, 72, 141, 46, 2; 601/37; 600/383
See application file for complete search history.

(56) References Cited

U.S. PATENT DOCUMENTS

| | | | |
|---|---|---|---|
| 4,745,100 A | 5/1988 | Gilbard et al. | 514/12 |
| 5,099,829 A * | 3/1992 | Wu | 601/46 |
| 6,275,735 B1 * | 8/2001 | Jarding et al. | 607/53 |
| 6,277,855 B1 | 8/2001 | Yerxa | 514/256 |
| 2003/0225041 A1 | 12/2003 | Nolan | |

OTHER PUBLICATIONS

Bron et al., Meibomian Gland Disease. Classification and Grading of Lid Changes; Eye; vol. 5; pp. 395–411; 1991.

Denton, et al., Ocular Infections: Update on Therapy, Therapy of Infectious Blepharitis; MD Consult—Journal Article, Opthalmology Clinics of North America; vol. 12—No. 1; Mar. 1999.

Driver et al., Meibomian Gland Dysfunction, Survey of Opthalmology; vol. 40, No. 5; Mar.–Apr. 1996.

Lipham, et al., A Histologic Analysis and Three–Dimensional Reconstruction of the Muscle of Riolan; The American Society of Opthalmic Plastic and Reconstructive Surgery, Inc.; vol. 18(2):pp. 93–98; 2002.

Mackie, Ian A., Riolan's Muscle: action and indications for botulinum toxin injection; Eye, vol. 14, pp. 347–352, 2000.

Mathers, et al., Assessment of the Tear Film with Tandem Scanning Confocal Microscopy, Cornea vol. 16(2); pp. 162–168, 1997.

Mathers, et al., Meibomian Gland Morphology and Tear Osmolarity: Changes with Accutane Therapy; Cornea, vol. 10(4); pp. 286–290, 1991.

Mathers, et al., Video Imaging of the Meibomian Gland, Arch Opthalmol, vol. 112, Apr. 1994.

Shimazaki, et al., Meibomian Gland Dysfunction in Patients with Sjögren Syndrome; Opthalmology; vol. 105, No. 8, Aug. 1998.

Seifert, et al., Vasoactive Intestinal Polypeptide (VIP) Innervation of the Human Eyelid Glands, Exp. Eye Res.; vol. 68, pp. 685–692, Article No. exer. 1999.0652 available online at http://www.idealibrary.com on IDEAL.

(Continued)

*Primary Examiner*—Jeffrey R. Jastrzab
*Assistant Examiner*—Alyssa M. Alter

(57) ABSTRACT

A method and apparatus are provided by which eyelid diseases may be treated and eyelid hygiene may be performed. In particular, the method and apparatus stimulate eyelid muscles and facial muscles, allowing stimulation of glandular eyelid components that allow optimization of the tear film and the ocular surface. In this manner, the symptoms associated with ocular irritation or with eyelid disorders may be treated by maintaining proper tear film composition.

10 Claims, 2 Drawing Sheets

OTHER PUBLICATIONS

Sirigu, et al., Human Meibomian Glands: The Ultrastructure of Acinar Cells as Viewd by Thin Section and Freeze–Fracture Transmission Electron Microscopies, Investigative Opthalmology & Visual Science, vol. 33, No. 7, Jun. 1992.

Stern, et al., The Pathology of Dry Eye: The Interaction Between the Ocular Surface and Lacrimal Glands; Cornea, vol. 17(6); pp. 584–589, 1998.

Yokoi, et al., Assessment of Meibomian Gland Function in Dry Eye Using Meibometry, Opthalmolog, vol. 117, No. 6, Jun. 1999.

Lipham, et al., A Histologic Analysis and Three–Dimensional Reconstruction of the Muscle of Riolan; The American Society of Opthalmic Plastic and Reconstructive Surgery, Inc.; vol. 18(2); pp. 93–98; 2002.

* cited by examiner

METHOD AND APPARATUS FOR PREVENTING AND TREATING EYELID PROBLEMS

BACKGROUND OF THE INVENTION

1. Field of the Invention

The present invention relates generally to the field of ophthalmology and, more specifically, to the field of eyelid hygiene and treatment.

2. Description of the Related Art

This section is intended to introduce the reader to aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of ophthalmology, a common patient complaint is of ocular irritation, such as dry-eye, a diagnosis characterized by burning, red eyes, irritation, itching, and vision fluctuations. Symptoms typically result from an insufficiently lubricated ocular surface which increases the shear forces associated with blinking and which reduces the ability of the ocular surface to respond to environmental challenges, such as wind, low humidity, and particulates. The label "dry-eye," however, may be a misnomer as aqueous tear production can be normal in patients with this diagnosis. Instead, dry-eye symptoms are commonly precipitated by a change in the composition of the tear film coating of the eye that may be in itself irritating or that may deviate from the tear film's optimal ocular surface properties, causing an increase in the rate of evaporation of the tear film.

In particular, a lipid component of the tear film may be either reduced or changed in composition, thereby increasing the rate of evaporation. These changes in the lipid layer are often the result of obstructive meibomian gland dysfunction (MGD), a form of posterior blepharitis that results in changes to the local eyelid margin. In particular, obstruction of the meibomian glands may decrease delivery of meibomian gland secretions, which comprise various oil and lipid components and which are typically expelled from the glands upon blinking.

The meibomian glands themselves are a row of enlarged sebaceous glands disposed along the lid margin posterior to the lid lashes. The meibomian glands are found on both the upper and lower lids and produce a holocrine lipid secretion that constitutes the surface layer of the preocular tear film. This lipid surface layer helps produce a smooth optical surface, reduces evaporation, and reduces contamination by skin surface lipids. Despite its importance, the lipid surface layer is believed to comprise only the upper 70 nanometers or so of the 7.0 micron thick tear film.

Structurally, the meibomian glands are generally straight tubules from which saccular acini project. Smooth and skeletal muscle fibers and elastic tissue is found around the acini. In addition, the muscle of Riolan and other periocular skeletal eye muscles are also associated with the glands. Fibers in the muscle of Riolan are arranged around the ducts leading to the orifices of the Meibomian glands and are believed to have a role in the expression of the meibomian gland secretions. In particular, combined movements within the Riolan muscle may compress the meibomian gland ductules, expressing their contents. The periocular eye muscles maintain line tone and the normal apposition of the eyelid margins to the ocular surface providing optimal application of the components of the tear film.

However, when a patient is afflicted with MGD, the meibomian glands may be plugged or partially plugged, typically with yellowish, solidified oil and lipids. In particular, the gland products themselves, i.e. lipids and oils, may solidify within the gland ducts plugging the ducts. Due to the plugging of the ducts, secretory product, as well as the relative bacterial counts, are built up within the gland and sufficient meibomian oils and lipids are not expressed into the tear film, increasing the relative counts of the normal flora of the eye. The solidification of gland products may occur for various reasons such as temperature sensitivity or melting point shifts, hormonal influences, variations in lipid composition, or infection.

Treatment for MGD comprises a regimen of lid hygiene. Typically applying warm compresses to the eyelids, massaging the eyelids, and washing the eyelid using a lid scrub are performed to express the contents of the meibomian glands. While such a regimen may be helpful, it may not be sufficient in acute cases of MGD. In addition, depending on the indications, antibiotics and steroids might also be employed in treatment. A more effective mechanism of lid hygiene, capable of unplugging even severely plugged ducts is therefore desired. The present invention addresses one or more of the concerns set forth above.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
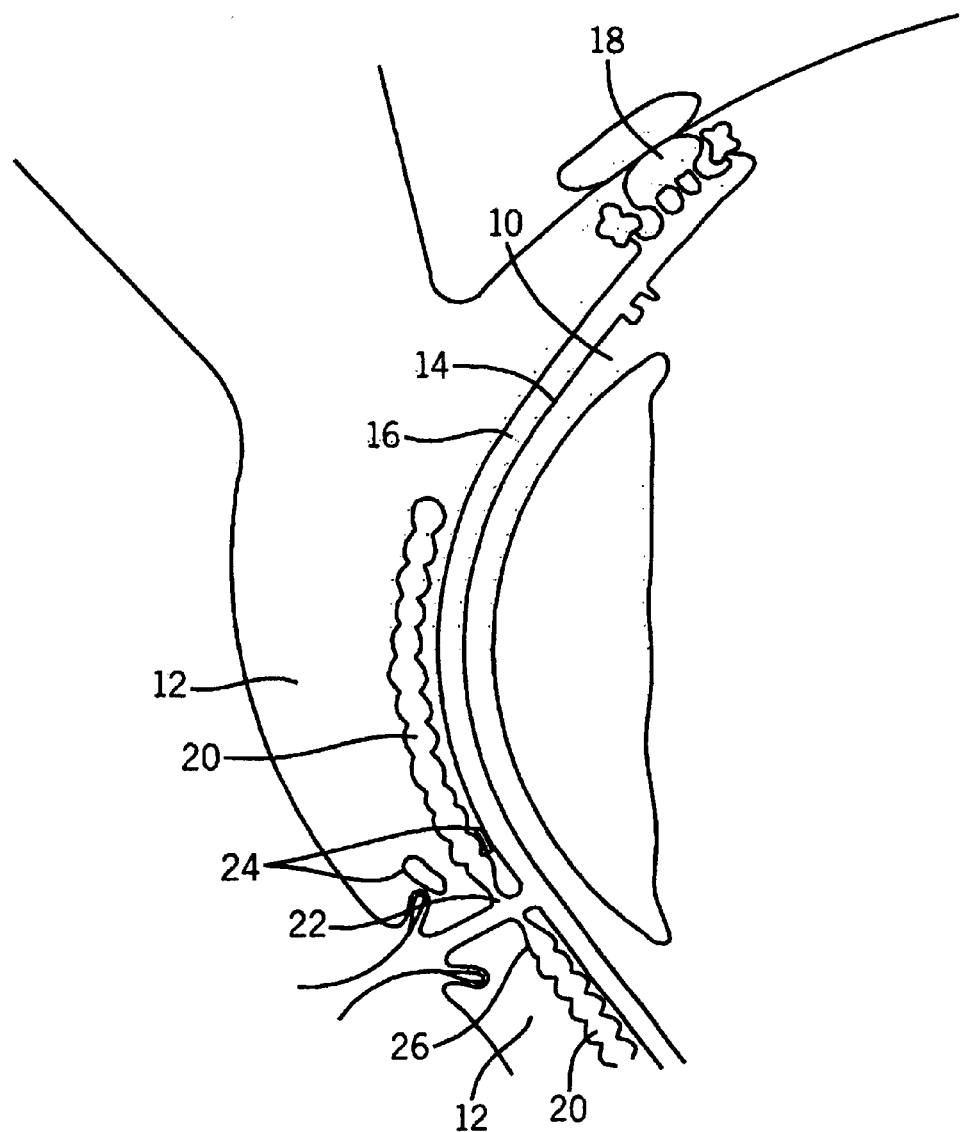
FIG. 1 is a cross-sectional, side-view depicting an eye and eyelids.

One or more specific embodiments of the present invention will be described below. Turning now to the drawings, and referring initially to FIG. 1, a cross-section of an eye 10 and associated eyelids 12 are depicted. The eye 10 comprises an ocular surface 14 which is in contact with a layer of tear film 16. The aqueous phase of the tear film is largely produced by the lacrimal glands 18. Other components of the tear film 16 are produced by various other glands, such as the goblet cells, the gland of Wolfring, and the glands of Krause, which are not depicted for simplicity.

A lipid component of the tear film 16 is produced by the meibomian glands 20. The orifices 22 of the meibomian glands 20 are located on the edges of the eyelids 12. The meibomian gland itself comprises various saclike acini which are surrounded by smooth muscle tissue and the muscle of Riolan 24 which are presumed to aid in the expression of the meibomian gland products.

Because of the involvement of the smooth muscle tissue and the muscle of Riolan in the expression of meibomian gland products, stimulation of the various muscle fibers may be employed to express the meibomian gland 20, expelling any obstructing plug 26 which obstructs the orifice 22 to allow the normal flow of meibomian gland secretory products. The obstructing plug 26 may be composed of hardened lipids and oils or cellular debris or some combination thereof.

Figure 2:
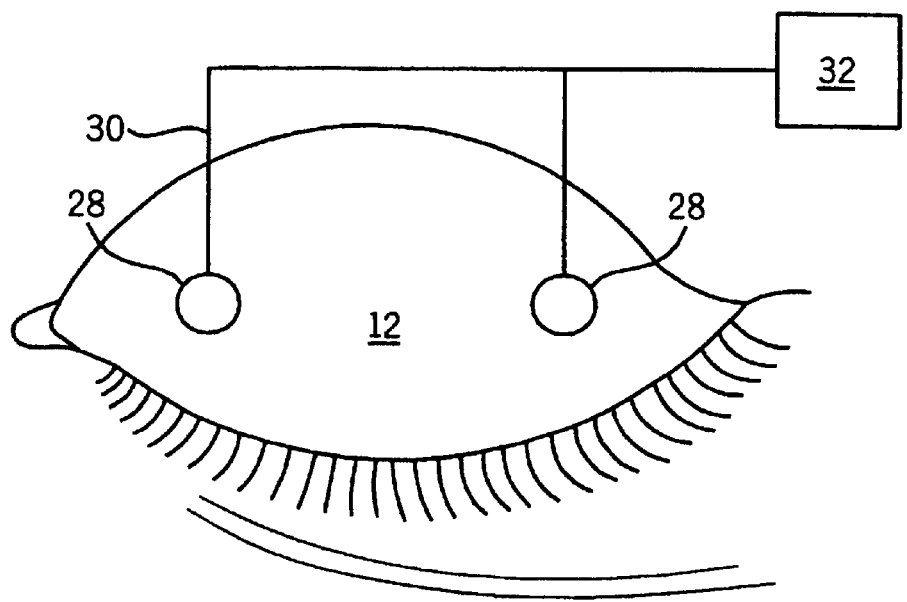
FIG. 2 is a front view of an upper and lower eyelid receiving electrical stimulation.

Stimulation of the appropriate muscles has been found to expel these obstructing plugs 26. For example, in one embodiment of the present invention, an low-intensity, pulsed electrical current is used to induce contraction of the muscle of Riolan 24 or other muscles associated with the meibomian gland 20 or eyelid 12. Referring now to FIG. 2, the use of an electrical current to stimulate muscle contraction is depicted. In particular, electrical contacts 28 are disposed upon the exterior surface of one of the eyelids 12. Lead wires 30 or an equivalent inductive mechanism connect the electrical contacts 28 to a power source 32. As one skilled in the art will realize, the electrical contacts 28 may be loose or may be fixed upon an applicator, such as a wand or other device, such that a constant distance is maintained and the lead wires 30 are not loose. Similarly, the electrical contacts 28 are sized such that they may be simultaneously disposed upon the eyelid 12 to stimulate contractions. In particular, the electrical contacts 28 are each sized to skin contact area of less than 1.5 cm$^2$. In one embodiment of the present invention the surface area of each contact 28 is approximately 1.14 cm$^2$.

An electrical current is provided by the power source 32 to the electrical contacts 28, thereby inducing muscular contractions within the eyelid 12. The resulting contractions act to expel any obstructing plugs 26 within the orifices 22 of the meibomian glands 20, allowing the free flow of the normal lipid secretory product. The induced contractions may also cause the secretion or expulsion of other additional beneficial tear film components. Additionally, the resulting stimulation has the added benefit of improving muscle tonus within the eyelid and surrounding facial muscles.

In a typical embodiment, the power supply 32 provides a direct current, typically comprising a pulse wave-form with a pulse basewidth of less than 60 microseconds and a pulse frequency less than or equal to 1 pulse per second. The voltage producing the current is less than or equal to 300 V. The current is generally less than or equal to 1.0 milliamp and is preferably less than or equal to 0.6 milliamps with a resulting power of 0.2 W or less. A current density of less than or equal to 2 milliamps/cm$^2$ and a power density of less than or equal to 3.0 watts/cm$^2$ typically result for the preferred ranges of current and contact 28 surface areas. While the depicted embodiment demonstrates the current being applied to the periocular muscles of the upper eyelid 12, the current may be applied to the periocular muscles of either eyelid 12 or, indeed, to other facial muscles associated with expression.

The application of the current itself may be applied from once a day to several times a day. Further, the applied current may vary between applications so long as an adequate massage or twitching of the eyelid 12 is achieved. The treatment may be continued as long as needed and may be used either as a treatment for obstructive MGD or as a preventative or maintenance measure.

Figure 3:
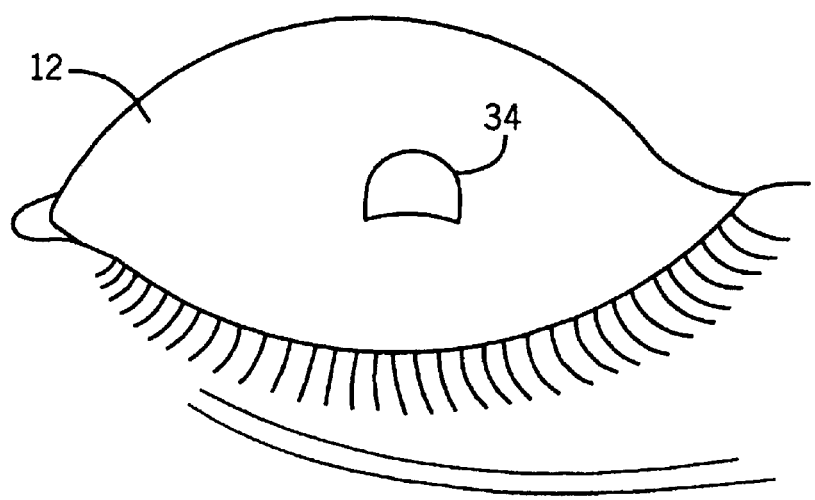
FIG. 3 is a front view of an upper and lower eyelid receiving chemical stimulation.

In addition, an alternative embodiment of the present invention, as depicted in FIG. 3, allows for the application of a chemical 34 to stimulate contraction of the muscles associated with the meibomian glands 20. The chemical 34 may be applied topically to the exterior to the eyelid, as depicted, or may alternatively be applied as an eyedrop, thereby stimulating the appropriate muscles, glands or cells from the interior surface of the eyelids 12.

In this embodiment, contraction of the muscles or glands may be accomplished by a variety of neurotransmitters, including various neuropeptides. One such peptide believed to be associated with the contraction of muscles associated with the meibomian glands 20 is vasoactive intestinal polypeptide (VIP). Application of a VIP containing compound upon the interior or exterior of the eyelids 12 may therefore be employed to stimulate muscle contraction as discussed above. In particular, such a treatment may be employed as needed at dosages sufficient to promote muscle contraction and clearance of any plugs 26 obstructing orifice 22 or as a preventative measure to prevent such plugs 26 from forming. One skilled in the art will recognize that other neuromuscular transmitters may also be employed as an active ingredient to achieve the same efficacy. Additionally, as discussed in regard to electrical stimulation, the secretion or expulsion of other beneficial tear film components and the improvement in tonus within the stimulated region may also result from the chemical stimulation.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method for treating eyelid disorders, the method comprising:

applying an electrical stimulus to one or more facial muscles associated with one or more eyelid glands; and promoting the expression of a tear film component from the one or more eyelid glands by application of the stimulus.

2. The method of claim 1, wherein applying the electrical stimulus comprises applying a direct current less than or equal to 1.0 milliamps.

3. The method of claim 1, wherein applying the stimulus to the one or more facial muscles comprises applying the stimulus to one or more periocular muscles.

4. The method of claim 3, wherein applying the stimulus to the one or more periocular muscles comprises applying the stimulus to one or more muscles of Riolan.

5. The method of claim 1, wherein promoting the expression of the tear film component from the one or more eyelid glands comprises promoting the expression of a lipid composition from one or more meibomian glands.

6. The method of claim 1, wherein applying the stimulus comprises:

disposing two or more electrical contacts upon an eyelid; and applying an electrical current to the eyelid via the two or more electrical contacts.

7. The method of claim 6, wherein the two or more electrical contacts are disposed a fixed distance apart upon an applicator.

8. The method of claim 1, wherein applying the stimulus comprises applying a direct current.

9. The method of claim 1, wherein applying the stimulus comprises applying a direct current having a current density of less than or equal to 2.0 milliamps/cm$^2$.

10. The method of claim 1, wherein applying the stimulus comprises applying a direct current having a pulse waveform.

* * * * *